United States Patent
Wang et al.

(10) Patent No.: US 11,538,586 B2
(45) Date of Patent: Dec. 27, 2022

(54) CLINICAL DECISION SUPPORT

(71) Applicant: International Business Machines Corporation, Armonk, NY (US)

(72) Inventors: Ke Wang, Beijing (CN); Jian Min Jiang, Beijing (CN); Bibo Hao, Beijing (CN); En Liang Xu, Beijing (CN); Yong Qin, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 105 days.

(21) Appl. No.: 16/405,047

(22) Filed: May 7, 2019

(65) Prior Publication Data
US 2020/0357514 A1    Nov. 12, 2020

(51) Int. Cl.
*G16H 50/20* (2018.01)
*G16H 10/60* (2018.01)
*G16H 70/20* (2018.01)
*G16H 80/00* (2018.01)
*G16H 20/10* (2018.01)

(52) U.S. Cl.
CPC ............. *G16H 50/20* (2018.01); *G16H 10/60* (2018.01); *G16H 70/20* (2018.01); *G16H 80/00* (2018.01); *G16H 20/10* (2018.01)

(58) Field of Classification Search
CPC ........ G16H 10/60; G16H 20/10; G16H 50/20; G16H 70/20; G16H 80/00
USPC .......................................................... 705/2
See application file for complete search history.

(56) References Cited

U.S. PATENT DOCUMENTS

| | | | |
|---|---|---|---|
| 2005/0131663 A1* | 6/2005 | Bangs | G16H 50/50 703/11 |
| 2012/0047105 A1* | 2/2012 | Saigal | G16Z 99/00 706/54 |
| 2013/0282396 A1 | 10/2013 | Lagor | |
| 2014/0025393 A1 | 1/2014 | Wang et al. | |
| 2015/0227701 A1* | 8/2015 | Nicolaas | G16H 50/20 705/2 |
| 2016/0092641 A1* | 3/2016 | Delaney | G16H 40/20 705/3 |
| 2016/0103960 A1 | 4/2016 | Hume et al. | |

(Continued)

OTHER PUBLICATIONS

Putora, P.M., Panje, C.M., Papachristofilou, A. et al. Objective consensus from decision trees. Radiat Oncol 9, 270 (2014). https://doi.org/10.1186/s13014-014-0270-y (Year: 2014).*

(Continued)

*Primary Examiner* — Jonathan Ng
*Assistant Examiner* — Bennett Stephen Erickson
(74) *Attorney, Agent, or Firm* — Patterson + Sheridan, LLP (57) ABSTRACT

A computer-implemented method for clinical decision support is provided according to an embodiment of the present disclosure. In the method, patient information can be obtained that comprises at least one clinical condition. A graph can be searched for at least one rule matching the at least one clinical condition. The graph represents a plurality of rule sets. The rule set comprises one or more rule. The rule can be indicated with a path comprising at least one first node and a second node. The first node can indicate a clinical condition, and the second node can indicate a clinical conclusion. Then, a clinical conclusion can be determined based on the at least one path in response that the at least one path matching the at least one clinical condition is searched out.

20 Claims, 8 Drawing Sheets

(56) References Cited

U.S. PATENT DOCUMENTS

| | | | | |
|---|---|---|---|---|
| 2016/0132648 | A1* | 5/2016 | Shah | G16H 70/20 |
| | | | | 705/2 |
| 2016/0283673 | A1* | 9/2016 | Chariot | G06F 16/24573 |
| 2017/0277841 | A1* | 9/2017 | Shankar | G16Z 99/00 |
| 2017/0277857 | A1* | 9/2017 | De La Torre | G16H 50/30 |
| 2017/0316324 | A1* | 11/2017 | Barrett | G06N 20/20 |
| 2017/0351819 | A1* | 12/2017 | Yamamoto | G06F 16/285 |
| 2019/0189287 | A1* | 6/2019 | Livesay | G16H 50/70 |
| 2019/0311810 | A1* | 10/2019 | Sevenster | G16H 50/70 |
| 2020/0004746 | A1* | 1/2020 | Randall | G06T 11/206 |

OTHER PUBLICATIONS

Putora, Paul Martin et al. "Objective consensus from decision trees." Radiation oncology (London, England) vol. 9 270. Dec. 5, 2014 , doi: 10.1186/s13014-014-0270-y (Year: 2014).*

Mei, et al. "Building Evidence Graph for Clinical Decision Support", viewed at <http://ceur-ws.org/Vol-1690/paper8.pdf>, 2016, 4 pages.

* cited by examiner

CLINICAL DECISION SUPPORT

BACKGROUND

The present disclosure relates to representations and processing of clinical data, and more specifically, to clinical decision support based on a graph representing a plurality of rule sets.

A clinical decision support system (CDSS) is a system that provides one or more of administrators, clinicians, patients, and the like, with clinical recommendations. The clinical recommendations are intelligently filtered and presented at appropriate times.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter.

According to an embodiment of the present disclosure, there is provided a computer-implemented method for clinical decision support based on a graph representing a plurality of rule sets. In the method, patient information can be obtained that comprises at least one clinical condition. A graph can be searched for at least one path matching the at least one clinical condition. The graph represents a plurality of rule sets. The rule set comprises one or more rule. The rule can be indicated with a path comprising at least one first node and a second node. The first node can indicate a clinical condition, and the second node can indicate a clinical conclusion. Then, a clinical conclusion can be determined based on the at least one path in response that the at least one path matching the at least one clinical condition is searched out.

According to another embodiment of the present disclosure, there is provided a system for clinical decision support based on a graph representing a plurality of rule sets. The system may comprise one or more processors, a memory coupled to at least one of the processors, and a set of computer program instructions stored in the memory. The set of computer program instructions may be executed by at least one of the processors to perform the above method.

According to an embodiment of the present disclosure, there is provided a computer program product for clinical decision support based on a graph representing a plurality of rule sets. The computer program product may comprise a computer readable storage medium having program instructions embodied therewith. The program instructions executable by a processor causes the processor to perform the above method.

In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

FIG. 7 (1) depicts an exemplary diagram of a graphical representation according to an embodiment of the present disclosure.

FIG. 7 (2) depicts an exemplary diagram of a graphical representation according to an embodiment of the present disclosure.

FIG. 7 (3) depicts a schematic diagram of a knowledge graph generated based on the graphical representations shown in FIG. 7(1) and FIG. 7 (2).

FIG. 10 (1) depicts an example for illustrating a process of clinical decision making using the knowledge graph shown in FIG. 9.

FIG. 10 (2) depicts another example for illustrating a process of clinical decision making using the knowledge graph shown in FIG. 9.

DETAILED DESCRIPTION

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
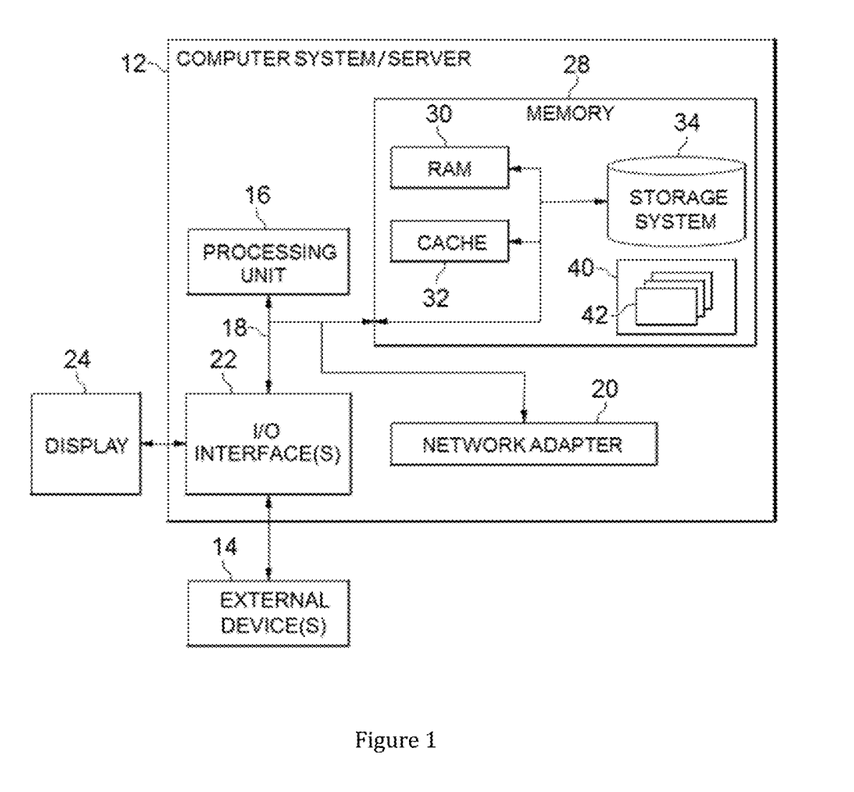
FIG. 1 depicts a cloud computing node according to an embodiment of the present disclosure.

Referring now to FIG. 1, a schematic of an example of a cloud computing node is shown. Cloud computing node 10 is only one example of a suitable cloud computing node and is not intended to suggest any limitation as to the scope of use or functionality of embodiments of the disclosure described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the disclosure as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
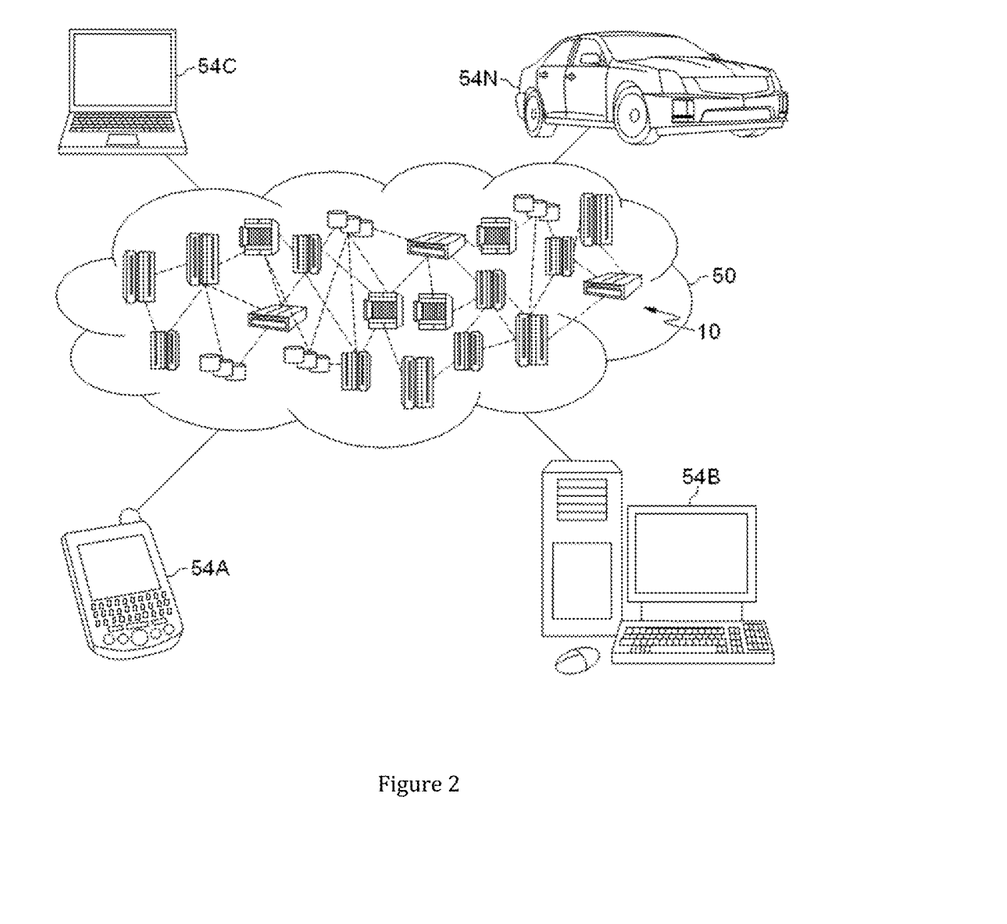
FIG. 2 depicts a cloud computing environment according to an embodiment of the present disclosure.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
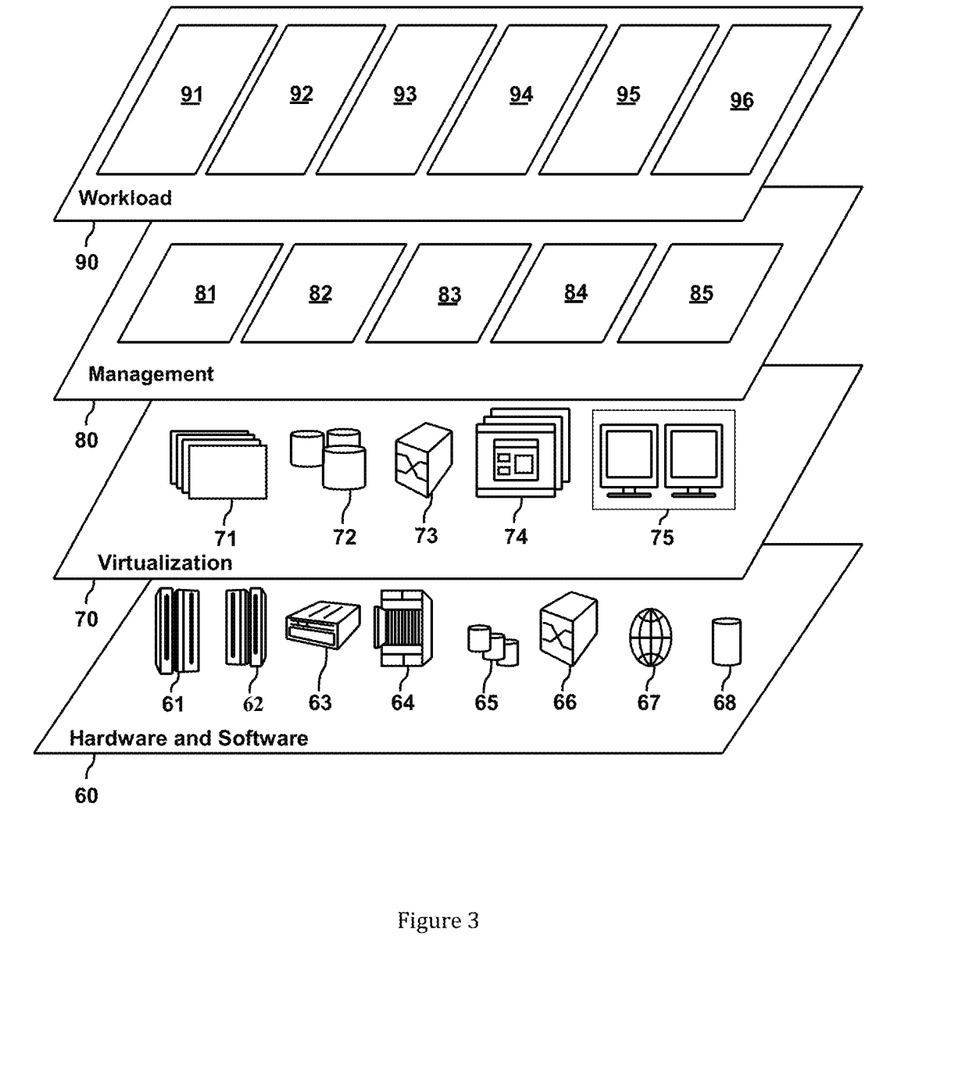
FIG. 3 depicts abstraction model layers according to an embodiment of the present disclosure.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and clinical decision support 96.

A Clinical decision support (CDS) is a key part of a clinical information system designed to aid clinician decision making during the process of care. While CDS can be delivered via a variety of media, including paper, the term CDS is most widely used for computer-based interventions delivered through the clinical information system. Common types of clinical decision support include drug-interaction checking, preventive care reminders and adverse drug event detection. There is substantial evidence to suggest that the clinical decision support system, when well designed and effectively used, can be powerful tools for improving the quality of patient care and preventing errors and omissions.

Generally, the clinical decision support is based on a single rule set from historical clinical knowledge or data. Therefore, a huge amount of rule sets can be stored for making clinical decision. Typically, these rule sets are stored separately, and can be implemented individually. As there may be a same clinical condition and/or a same therapy scheme in different rule sets, for example, a plurality of hypertension complications relate to a same symptom of abnormal blood pressure and/or hypertension therapy scheme, the different rule sets can be merged according to embodiments of the present disclosure.

In some embodiments, the individual rule set from the historical clinical data can be combined to generate a graph. The graph is the knowledge graph. The generating process for the knowledge graph is a predefined process based on the historical clinical data. After predefined, the knowledge graph can be stored in a memory and/or an online system for searching, retrieval and other purposes in later use.

Further, the knowledge graph can be generated based on a plurality of graphical representations. The graphical representation represents the rule set. In some embodiments, two or more first nodes in different graphical representations indicating a same clinical condition can be combined. Moreover, two or more second nodes in different graphical representations indicating a same clinical conclusion can be combined.

Figure 4:
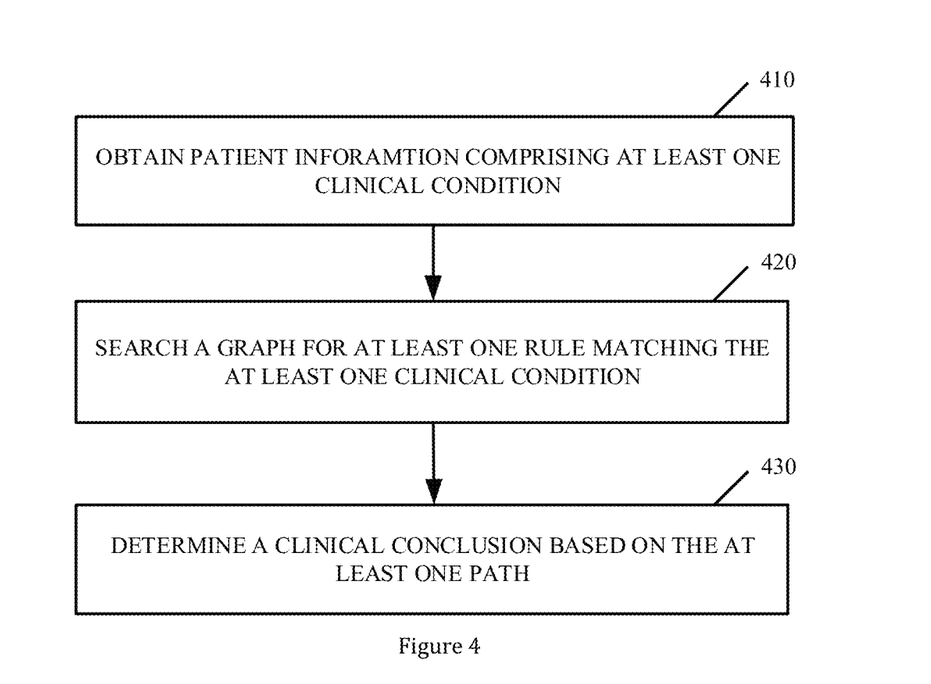
FIG. 4 depicts a schematic flowchart of a method for clinical decision support according to an embodiment of the present disclosure.

With reference now to FIG. 4, it shows a schematic flowchart of a method for clinical decision support based on a knowledge graph representing a plurality of rule sets according to an embodiment of the present disclosure. The embodiment can be implemented for treatment and diagnosis. The embodiment will be described in detail below in conjunction with the Figures.

Figure 5:
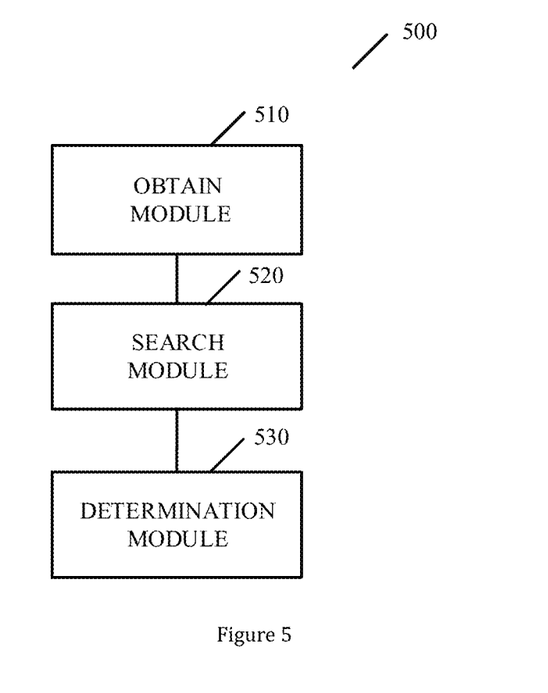
FIG. 5 depicts a schematic diagram of an apparatus for clinical decision support in which the method shown in FIG. 4 is implemented.

It should be noted that the processing of clinical decision support according to embodiments of this disclosure could be implemented by an apparatus 500 for clinical decision support in FIG. 5. As FIG. 5 shows, the apparatus 500 may comprise an obtain module 510, a search module 520, and a determination module 530. The respective modules of the apparatus 500 could be implemented by the computer system/server 12 of FIG. 1.

As shown in FIG. 4, at block 410, the obtain module 510 obtains patient information. The patient information comprises at least one clinical condition.

In some embodiments, a physician may ask a patient for the patient information. Then, the physician may input the collected patient information to the obtain module 510.

In an embodiment for diagnosis, the clinical condition may comprise a patient symptom. The patient symptom may include, but not limited to, yellow mucus, clear mucus, fever, headache, sneeze, acute cough, sore throat, or the like.

Moreover, in an embodiment for treatment, the patient information may further comprise a disease of the patient. The disease, for example, includes, but not limited to, hypertension, myocardial infarction, angina, diabetes, chronic kidney disease, or the like. Moreover, the disease may also include complications, such as hypertension with myocardial infarction, diabetes with chronic kidney disease, or the like. In this case, the clinical condition can comprise level of the disease, which can be obtained through biological measurements. For example, level of hypertension can be obtained according to measurement of blood pressure.

Then, at block 420, the search module 520 searches a knowledge graph for at least one path matching the at least one clinical condition. The knowledge graph is based on historical clinical data. The knowledge graph represents a plurality of rule sets. The respective rule set comprises one or more rule. The rule comprises at least one clinical condition and a clinical conclusion. In the knowledge graph, the rule may be indicated with a path. The path includes at least one first node and a second node. The first node indicates the clinical condition. The second node indicates the clinical conclusion.

In the embodiment for diagnosis, the clinical conclusion may be a diagnostic result, for example, a kind of disease. In some embodiments, the diagnostic result may include, but not limited to, acute sinusitis, allergic rhinitis, cold, or the like. In this situation, in the knowledge graph, the first node may indicate the patient symptom, and the second node may indicate the diagnostic result.

Moreover, in the embodiment for treatment, the clinical conclusion may be a therapeutic scheme, for example, taking medicine, infusion of fluids, surgery, transferring to another medical institution, or the like. In this case, the rule may further include a patient disease. That is, the rule comprises a patient disease, at least one clinical condition (such as, level of the disease), and a clinical conclusion (such as, therapeutic scheme). In the knowledge graph, the rule can be indicated by a path including a start node, at least one first node and the second node. The start node may indicate the patient disease, the first node may indicate the level of the disease, and the second node may indicate the therapeutic scheme.

Figure 6:
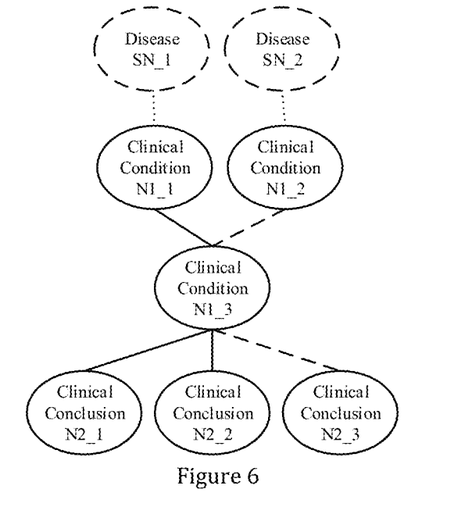
FIG. 6 depicts a schematic diagram of a knowledge graph according to an embodiment of the present disclosure.
Figure 7:
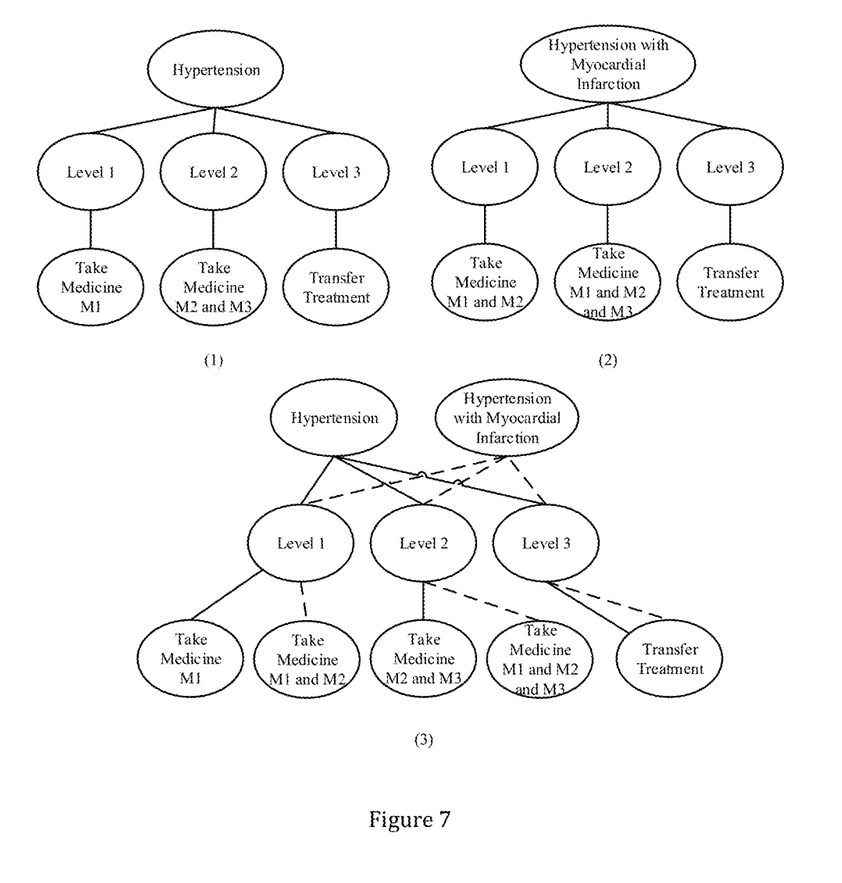

FIG. 6 shows a schematic diagram of a knowledge graph according to an embodiment of the present disclosure. As shown in FIG. 6, in the knowledge graph, ovals indicated by Clinical Condition N1_1, Clinical Condition N1_2, and Clinical Condition N1_3 represent the first nodes, and ovals indicated by Clinical Conclusion N2_1, Clinical Conclusion N2_2, and Clinical Conclusion N2_3 represent the second nodes. It can be noted that shape of nodes is not limited to oval, while other appropriate shape can also be used to indicate the nodes. Moreover, different type of nodes can also be identified with different size or shape. As can be seen from FIG. 6, for diagnosis purpose, the knowledge graph comprises three paths. The first path includes Clinical Condition N1_1, Clinical Condition N1_3, and Clinical Conclusion N2_1 which are coupled together with solid lines. The second path includes Clinical Condition N1_1, Clinical Condition N1_3, and Clinical Conclusion N2_2 which are coupled together with solid lines. The third path includes Clinical Condition N1_2, Clinical Condition N1_3, and Clinical Conclusion N2_3 which are coupled together with broken lines.

In some embodiment, the respective rules in a same rule set may share an initial node, for example, a beginning one of the at least one first node (in a diagnosis process). It can be noted that different graphical representations (different rule sets) can use different indicators, for example, different colors, different line shapes, or the like. As FIG. 6 shows, the first rule set includes a first rule indicated by the first path and a second rule indicated by the second path, the first path and the second path sharing an initial first node Clinical Condition N1_1. The second rule set only includes a third rule indicated by the third path with another graphical representation. On the other hand, as Clinical Condition N1_1, Clinical Condition N1_3, and Clinical Conclusion N2_3 are coupled by different kinds of connection lines, they cannot form a single rule.

In another embodiment, for treatment purpose, as shown in FIG. 6, the knowledge graph may further comprise two start nodes, Disease SN_1 and Disease SN_2. The start node Disease SN_1 is coupled to the first node Clinical Condition N1_1. The start node Disease SN_2 is coupled to the first node Clinical Condition N1_2. In this case, the knowledge graph may comprise three paths. A first path includes Disease SN_1, Clinical Condition N1_1, Clinical Condition N1_3, and Clinical Conclusion N2_1. A second path includes Disease SN_1, Clinical Condition N1_1, Clinical Condition N1_3, and Clinical Conclusion N2_2. A third path includes Disease SN_2, Clinical Condition N1_2, Clinical Condition N1_3, and Clinical Conclusion N2_3. The first path and the second path belong to a same rule set as they share an initial node (i.e., the start node Disease SN_1). The third path belongs to another rule set.

As above described, in a diagnosis embodiment, if there are two or more rules in a single rule set, the respective rule may have a same initial first node, i.e., a clinical condition. In a treatment embodiment, if there are two or more rules in a single rule set, the respective rules may a same start node, i.e., a same disease. Herein, the initial first node and the initial start node in both cases can be referred to as the initial node. Moreover, it can be understood that, there may be two or more rules having a same clinical conclusion, that is, a second node, i.e., a diagnosis result, or a therapeutic scheme. Specific details may not be described herein.

In a further embodiment, the connection lines may be identified with edge attribute to express priorities of the path. For example, the connection line between Clinical Condition N1_3 and Clinical Conclusion N2_1 and the connection line between Clinical Condition N1_3 and Clinical Conclusion N2_2 can be identified with prices, treatment effect, or the like.

In some embodiments, the knowledge graph can be generated based on a plurality of graphical representations. The graphical representation represents the rule set. In a further embodiment, the graph can be generated by at least one of the followings: combining two or more first nodes in different graphical representations indicating a same clinical condition, and combining two or more second nodes in different graphical representations indicating a same clinical conclusion.

Following shows an example for generating a knowledge graph for treatment decision making according to an embodiment of the present disclosure. FIG. 7 (1) shows an exemplary diagram of a graphical representation associated with Hypertension according to an embodiment of the present disclosure. FIG. 7 (2) shows an exemplary diagram of a graphical representation associated with Hypertension with Myocardial Infarction according to an embodiment of the present disclosure.

As shown in FIG. 7 (1), a first graphical representation for hypertension is presented. Based on biological measurements for blood pressure, hypertension may comprise three levels, Level 1, Level 2, and Level 3. For example, Level 1 refers to a systolic blood pressure SBP having a range between 140 to 159 mmHg$^2$ and a diastolic blood pressure DBP having a range between 90 to 99 mmHg$^2$. Level 2 refers to a SBP having a range from 160 to 179 mmHg$^2$ and a DBP having a range between 100 to 109 mmHg$^2$. Moreover, Level 3 refers to a SBP higher than 180 mmHg$^2$ and a DBP higher than 110 mmHg$^2$. As can be seen from FIG. 7 (1), corresponding to Level 1, the clinical conclusion can be taking Medicine M1. Corresponding to Level 2, the clinical conclusion can be taking Medicine M2 and M3. Moreover, corresponding to Level 3, the clinical conclusion can be transferring treatment to another clinical institute. It can be noted that the specific medicines are any suitable medicines, which are not limited hereto.

As shown in FIG. 7 (2), a second graphical representation for hypertension with myocardial infarction is presented. As described above, hypertension with myocardial infarction is a hypertension complication. The hypertension with myocardial infarction thus may also comprise the three levels based on blood pressure measurement. Corresponding to Level 1, the clinical conclusion can be taking Medicine M1 and M2. Corresponding to Level 2, the clinical conclusion can be taking Medicine M1, M2 and M3. Moreover, corresponding to Level 3, the clinical conclusion can be transferring treatment to another clinical institute.

It can be seen that, though the Diseases in the two graphical representations are different, in both graphical representations, the first nodes Level 1 indicate a same blood pressure range, the first nodes Level 2 indicate a same blood pressure range, and the first nodes Level 3 indicate a same blood pressure range. Therefore, such first nodes can be combined respectively as FIG. 7(3) shows.

FIG. 7(3) shows a schematic diagram of a knowledge graph generated based on the graphical representations shown in FIG. 7(1) and FIG. 7 (2). As FIG. 7 (3) shows, the first nodes Level 1 in both graphical representations are combined. The first nodes Level 2 in both graphical representations are combined. The first nodes Level 3 in both graphical representations are combined.

Moreover, the second nodes Transfer Treatment in both graphical representations indicate a same clinical conclusion. Therefore, the second nodes Transfer Treatment can be combined in FIG. 7(3).

As described above, different graphical representations may use different indicators, such as, different connection line shapes and/or different colors. As shown in FIG. 7 (3), the connection lines in the first graphical representations are solid lines, which may also be identified with a kind of color. The connection lines in the second graphical representations are broken lines, which may also be identified with another kind of color.

Furthermore, in an exemplary clinical situation, the physician may decide to use a medicine A for a patient, then use a medicine B if the patient was not getting better after taking the medicine A in a time period, and then use the medicine A again if the patient was still not getting better after taking the medicine B in another time period. Such clinical situation can also be represented by the knowledge graph according to embodiments of the present disclosure. For example, several nodes and the corresponding connection lines may form a loop in the knowledge graph. It can be understood that the knowledge graph can render a loop which cannot be represented by a decision tree.

In some embodiments, the clinical conclusion in a rule can also be the clinical condition in another rule. That is, the second node in the path can be considered as the first node in another path. For example, if a patient do not recover for a week after taking a medicine, such medicine and the not recovery condition can be clinical conditions for further treatment (i.e., another rule), thus another clinical conclusion can be obtained. Furthermore, several of the clinical conditions can form a loop via the respective connection lines in the knowledge graph.

Figure 8:
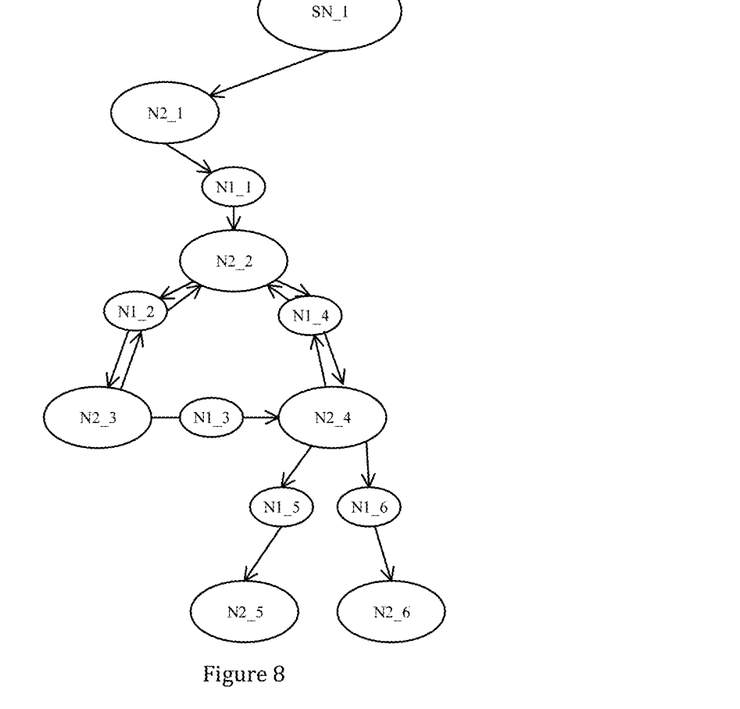
FIG. 8 depicts an exemplary diagram of a knowledge graph according to an embodiment of the present disclosure.

FIG. 8 shows an exemplary diagram of a knowledge graph according to an embodiment of the present disclosure. As shown in FIG. 8, a start node SN_1 is indicated with a large size oval. First nodes N1_1, N1_2, N1_3, N1_4, N1_5, and N1_6 are indicated with small size ovals. Second nodes N2_1, N2_2, N2_3, N2_4, N2_5, and N2_6 are indicated with medium size ovals. The nodes N2_2, N1_2, N2_3, N1_3, N2_4, and N1_4, and the respective connection lines form a loop. In an embodiment, a connection line with arrowhead in the knowledge represent an orientation of clinical decision process.

For an example, assume the start node SN_1 indicates a Disease of chronic obstructive pulmonary disease COPD.

The second node N2_1 indicates taking long acting muscarinic antagonist LAMA. The first node N1_1 indicates patient's condition worsened. The second node N2_2 indicates taking LAMA and long acting beta2 agonist LABA. The first node N1_2 indicates patient's condition worsened. The second node N2_3 indicates taking LABA and inhaled corticosteroid ICS. The first node N1_3 indicates patient's condition worsened. The second node N2_4 indicates taking LAMA, LABA and ICS. The first node N1_5 indicates chronic bronchitis. The second node N2_5 indicates taking Roflumilast. The first node N1_6 indicates smoking history. The second node N2_6 indicates taking Macrolipid antibiotics.

In this example, there are a plurality of paths in the knowledge graph. Path 1 comprises SN_1 and N2_2, wherein the disease can be considered as a clinical condition. Path 2 comprises SN_1, N2_1, N1_1, and N2_2, wherein N2_1 is a clinical condition rather than a clinical conclusion. Path 3 comprises SN_1, N2_1, N1_1, N2_2, N1_2, and N2_3, wherein N2_1 and N2_2 are clinical conditions and N2_3 is clinical conclusions. Path 4 comprises SN_1, N2_1, N1_1, N2_2, N1_2, N2_3, N1_2, and N2_2, wherein N2_2, N1_2, N2_3 form a loop, N2_1 and N2_3 are clinical conditions, N2_2 is both a clinical condition and a clinical conclusion. Other paths can be determined based on the knowledge graph, and not be described in detail herein.

Figure 9:
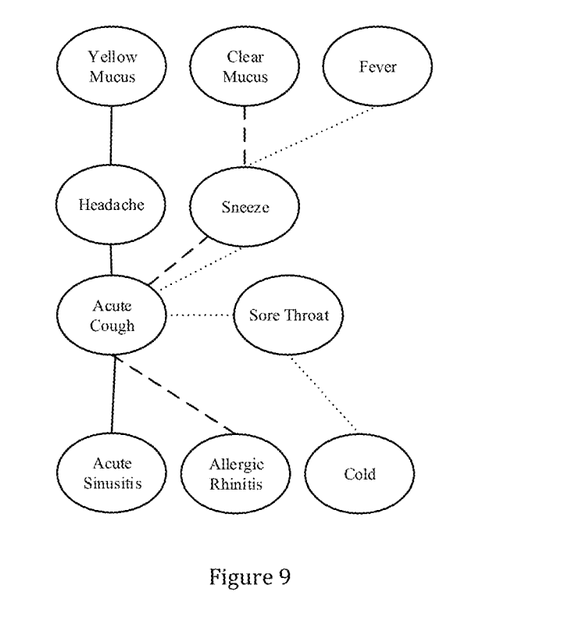
FIG. 9 depicts another exemplary diagram of a knowledge graph according to an embodiment of the present disclosure.
Figure 10:
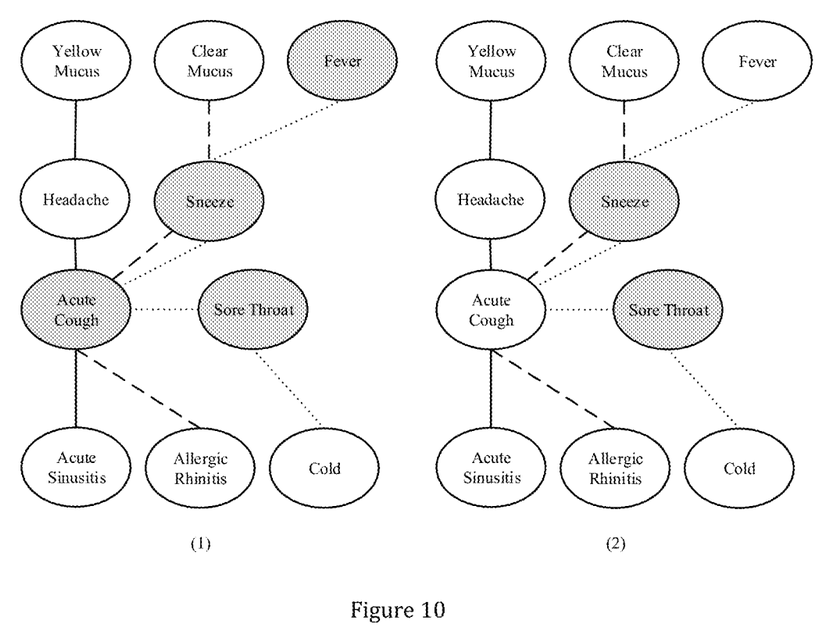

Moreover, FIG. 9 shows another exemplary diagram of a knowledge graph according to an embodiment of the present disclosure. As shown in FIG. 9, the knowledge graph is configured to make diagnosis decision, which comprises three rule sets. The respective rule set comprises only one rule, and each rule is identified with a path. A first path, indicated with solid lines, includes Yellow Mucus, Headache, Acute Cough, and Acute Sinusitis. A second path, indicated with broken lines, includes Clear Mucus, Sneeze, Acute Cough, and Allergic Rhinitis A third path, indicated with pointed lines, includes Fever, Sneeze, Acute Cough, Sore Throat, and Cold.

At block 430, the determination module 530 determines a clinical conclusion based on the at least one path in response that the at least one path matching the at least one clinical condition is searched out. For example, the determination module 530 may further prompt the determined clinical conclusion to the physician.

FIG. 10 (1) shows an example for illustrating a process of diagnosis decision making using the knowledge graph shown in FIG. 9. In this example, the physician asks the patient about clinical symptoms. The patient tells the physician that he or she had a fever, sneeze, acute cough and sore throat. Then, the physician inputs these symptoms to the obtain module 520. In some embodiments, the first nodes associated with these symptoms can be highlighted, marked with a unique color, or identified in other ways. As FIG. 10 (1) shows, the associated first nodes are identified in shadow. Therefore, the determination module 530 may identify a path comprising the associated first nodes. In this case, the determination module 530 may identify the third path including Fever, Sneeze, Acute Cough, Sore Throat, and Cold. Then, the determination module 530 may determine that the clinical conclusion is Cold based on the third path. That is, the determination module 530 may determine the patient got a cold. Therefore, the physician may prescribe based on the determination result from the clinical decision support.

In some other embodiments, the determination module 530 may identify a plurality of paths in the knowledge graph based on the patient information, in response that a plurality of rules matching the plurality of clinical conditions are searched out. Then, the determination module 530 may prompt, for each path, a further first node in the path which indicates a further clinical condition not comprised in the patient information. In response to obtaining subsequent patient information comprising the further clinical condition, the determination module 530 may determine the path out of the at least one path. Moreover, the determination module 530 may determine the clinical conclusion based on the determined path.

FIG. 10 (2) shows an example for illustrating a process of diagnosis decision making using the knowledge graph shown in FIG. 9. In this example, the patient tells the physician that the clinical symptoms are sneeze and sore throat. The physician inputs such symptoms to the obtain module 530. Similar with the example shown in FIG. 10 (1), the first nodes associated to these symptoms are identified in shadow. Therefore, the determination module 530 may determine two paths including the associated first nodes, which are the second path and the third path. Then, the determination module 530 may prompt a further first node in the path which indicates a further clinical condition not comprised in the patient information. For example, the determination module 530 may prompt the first nodes indicating Clear Mucus, Fever, and Acute Cough. After that, the obtain module 520 may obtain subsequent patient information. For example, the physician may further ask the patient whether he or she has the symptoms of Clear Mucus, Fever, or Acute Cough. If the obtain module 520 obtains clinical condition related to Clear Mucus and Acute Cough, the determination module 530 may identify the second path among the paths, and then determine the clinical conclusion is Allergic Rhinitis based on the identified second path. On the other hand, if the obtain module 520 obtains clinical condition related to Fever and Acute Cough, the determination module 530 may identify the third path among the paths, and then determine the clinical conclusion is Cold based on the identified third path. Moreover, if the obtain module 520 obtains clinical condition related to Clear Mucus, Fever, or Acute Cough, the determination module 530 may identify both the second path and the third path, and determine the clinical conclusion is both Allergic Rhinitis and Cold.

In a further embodiment, the determination module 530 may determine more than one clinical conclusion and prompt the determined clinical conclusions to the physician. In this case, the physician may choose one of the clinical conclusions according to experience and/or specific patient condition.

Moreover, in an embodiment, the knowledge graph can be modified with improvement of clinical technique based on updated clinical rules, for example, condition, clinical conclusion, and/or disease. In some embodiments, the knowledge graph can be modified by adding at least one path to the knowledge graph and/or removing at least one path from the knowledge graph. For example, when a physician obtains new rules, the physician may add new first nodes, second nodes, and/or start nodes and corresponding connection lines directly on the knowledge graph. Otherwise, when a physician finds an existing rule is not correct in the knowledge graph, the physician may also remove existing first nodes, second nodes, and/or start nodes and corresponding connection lines directly on the knowledge graph. Therefore, the knowledge graph can be updated more conveniently.

Embodiments of the present disclosure provide a method for clinical decision support for diagnosis and/or treatment based on a knowledge graph representing a plurality of rule sets. Storage space for storing the huge amount of rule sets can be saved, as same clinical condition and/or clinical conclusion can be combined. Moreover, it is easy to modify the rule sets without complicated compiling.

Additionally, in some embodiments of the disclosure, a system for clinical decision support can be provided. The apparatus may comprise one or more processors, a memory coupled to at least one of the processors, and a set of computer program instructions stored in the memory. The set of computer program instructions may be executed by at least one of the processors to implement the method shown in FIG. 4. In the method, patient information can be obtained that comprises at least one clinical condition. A graph can be searched for at least one path matching the at least one clinical condition. The graph represents a plurality of rule sets. The rule set comprises one or more rule. The rule can be indicated with a path comprising at least one first node and a second node. The first node can indicate a clinical condition, and the second node can indicate a clinical conclusion. Then, a clinical conclusion can be determined based on the at least one path in response that the at least one path matching the at least one clinical condition is searched out.

In some other embodiments of the disclosure, a computer program product for clinical decision support can be provided. The computer program product may comprise a computer readable storage medium having program instructions embodied therewith. The program instructions, when executed by a processor, cause the processor to implement the method shown in FIG. 4. In the method, patient information can be obtained that comprises at least one clinical condition. A graph can be searched for at least one rule matching the at least one clinical condition. The graph represents a plurality of rule sets. The rule set comprises one or more rule. The rule can be indicated with a path comprising at least one first node and a second node. The first node can indicate a clinical condition, and the second node can indicate a clinical conclusion. Then, a clinical conclusion can be determined based on the at least one path in response that the at least one path matching the at least one clinical condition is searched out.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
    receiving a plurality of rule sets, each respective rule set comprising one or more respective rules, wherein at least one rule of at least one of the plurality of rule sets indicates a clinical condition and a clinical conclusion;
    generating a combined graph including at least one loop based on the plurality of rule sets, wherein a first rule of at least one of the plurality of rule sets is indicated with a path comprising at least one first node and a second node, the at least one first node indicating a clinical condition and the second node indicating a clinical conclusion, and wherein generating the graph comprises:
        creating a node, in a first graphical representation, for a first clinical condition specified in a first rule set, wherein the first graphical representation further includes a first path corresponding to a first rule in the first rule set, and wherein the first path is associated with a first edge attribute indicating a priority of the first path based at least in part on a price associated with the first path;
        creating a node, in a second graphical representation, for a second clinical condition specified in a second rule set, wherein the second graphical representation further includes a second path corresponding to a second rule in the second rule set, and wherein the second path is associated with a second edge attribute indicating a priority of the second path based at least in part on a price associated with the second path; and
        upon determining that the first and second clinical conditions represented by the node in the first graphical representation and the node in the second graphical representation match, generating the combined graph by:
            combining the node, from the first graphical representation, for the first clinical condition and the node, from the second graphical representation, for the second clinical condition to create a single combined node in the combined graph to represent both the node from the first graphical representation and the node from the second graphical representation, and
            adding the first and second paths to the combined graph by adding one or more edges, in the combined graph, connecting to the combined node, wherein the combined graph distinguishes between the first and second rule sets by depicting the first path using a first color and the second path using a second color;
    obtaining, by operation of one or more processors, patient information comprising at least one clinical condition;
    searching, by operation of one or more processors, the graph based on the at least one clinical condition; and
    upon determining that at least one path matching the at least one clinical condition is found in the combined graph:
        highlighting, in the combined graph, one or more nodes associated with the at least one path; and
        determining, by one or more processors, a clinical conclusion based on the at least one path.

2. The method according to claim 1, wherein the combined graph is generated based on a plurality of graphical representations, wherein each of the plurality of graphical representations represents a respective rule set of the plurality of rule sets.

3. The method according to claim 2, wherein generating the combined graph further comprises:
    combining, by operation of one or more processors, two or more second nodes in different graphical representations indicating a same clinical conclusion.

4. The method according to claim 1, wherein determining the clinical conclusion comprises:
    prompting, for each of the at least one path, a further first node in the path which indicates a further clinical condition not comprised in the patient information;
    in response to obtaining subsequent patient information comprising the further clinical condition, determining a path from the at least one path; and determining the clinical conclusion based on the determined path.

5. The method according to claim 1, further comprising:
modifying, by one or more processors, the combined graph, based on updated clinical rule, comprising:
adding at least one path to the combined graph; and
removing at least one path from the combined graph.

6. The method according to claim 1, wherein the at least one first node comprises a plurality of first nodes, and some of the first nodes form a loop via respective connection lines.

7. The method according to claim 1, wherein the clinical condition is a patient symptom and the clinical conclusion is a diagnosis result.

8. The method according to claim 1, wherein the patient information further comprises a disease, and the path further comprises a start node, the start node indicating a disease; and
wherein the clinical condition is a level of the disease, and the clinical conclusion is a therapeutic scheme.

9. The method according to claim 1, wherein the rule set comprises two or more rules, and the respective rules have a same initial node and/or a same second node.

10. A system, comprising:
one or more processors;
a memory coupled to at least one of the processors; and
a set of computer program instructions stored in the memory and executed by at least one of the processors in order to perform actions of:
receiving a plurality of rule sets, each respective rule set comprising one or more respective rules, wherein at least one rule of at least one of the plurality of rule sets indicates a clinical condition and a clinical conclusion;
generating a combined graph including at least one loop based on the plurality of rule sets, wherein a first rule of at least one of the plurality of rule sets is indicated with a path comprising at least one first node and a second node, the at least one first node indicating a clinical condition and the second node indicating a clinical conclusion, and wherein generating the graph comprises:
creating a node, in a first graphical representation, for a first clinical condition specified in a first rule set, wherein the first graphical representation further includes a first path corresponding to a first rule in the first rule set, and wherein the first path is associated with a first edge attribute indicating a priority of the first path based at least in part on a price associated with the first path;
creating a node, in a second graphical representation, for a second clinical condition specified in a second rule set, wherein the second graphical representation further includes a second path corresponding to a second rule in the second rule set, and wherein the second path is associated with a second edge attribute indicating a priority of the second path based at least in part on a price associated with the second path; and
upon determining that the first and second clinical conditions represented by the node in the first graphical representation and the node in the second graphical representation match, generating the combined graph by:
combining the node, from the first graphical representation, for the first clinical condition and the node, from the second graphical representation, for the second clinical condition to create a single combined node in the combined graph to represent both the node from the first graphical representation and the node from the second graphical representation, and
adding the first and second paths to the combined graph by adding one or more edges, in the combined graph, connecting to the combined node, wherein the combined graph distinguishes between the first and second rule sets by depicting the first path using a first color and the second path using a second color;
obtaining patient information comprising at least one clinical condition;
searching the combined graph based on the at least one clinical condition; and
upon determining that at least one path matching the at least one clinical condition is found in the combined graph:
highlighting, in the combined graph, one or more nodes associated with the at least one path; and
determining a clinical conclusion based on the at least one path.

11. The system according to claim 10, wherein the combined graph is generated based on a plurality of graphical representations, wherein each of the plurality of graphical representations represents a respective rule set of the plurality of rule sets.

12. The system according to claim 11, wherein generating the combined graph further comprises:
combining two or more second nodes in different graphical representations indicating a same clinical conclusion.

13. The system according to claim 10, wherein the set of computer program instructions when executed performs actions of:
prompting, for each of the at least one path, a further first node in the path which indicates a further clinical condition not comprised in the patient information;
in response to obtaining subsequent patient information comprising the further clinical condition, determining a path from the at least one path; and
determining the clinical conclusion based on the determined path.

14. The system according to claim 10, wherein the at least one first node comprises a plurality of first nodes, and some of the first nodes form a loop via respective connection lines.

15. The system according to claim 10, wherein the clinical condition is a patient symptom and the clinical conclusion is a diagnosis result.

16. The system according to claim 10, wherein the patient information further comprises a disease, and the path further comprises a start node, the start node indicating a disease; and
wherein the clinical condition is a level of the disease, and the clinical conclusion is a therapeutic scheme.

17. A computer program product, comprising a computer readable storage medium having program instructions embodied therewith, the program instructions executable by a processor to cause the processor to:
receive a plurality of rule sets, each respective rule set comprising one or more respective rules, wherein at least one rule of at least one of the plurality of rule sets indicates a clinical condition and a clinical conclusion;
generate a combined graph including at least one loop based on the plurality of rule sets, wherein a first rule of at least one of the plurality of rule sets is indicated with a path comprising at least one first node and a second node, the at least one first node indicating a clinical condition and the second node indicating a clinical conclusion, and wherein generating the combined graph comprises:
- creating a node, in a first graphical representation, for a first clinical condition specified in a first rule set, wherein the first graphical representation further includes a first path corresponding to a first rule in the first rule set, and wherein the first path is associated with a first edge attribute indicating a priority of the first path based at least in part on a price associated with the first path;
- creating a node, in a second graphical representation, for a second clinical condition specified in a second rule set, wherein the second graphical representation further includes a second path corresponding to a second rule in the second rule set, and wherein the second path is associated with a second edge attribute indicating a priority of the second path based at least in part on a price associated with the second path; and
- upon determining that the first and second clinical conditions represented by the node in the first graphical representation and the node in the second graphical representation match, generating the combined graph by:
  - combining the node, from the first graphical representation, for the first clinical condition and the node, from the second graphical representation, for the second clinical condition to create a single combined node in the combined graph to represent both the node from the first graphical representation and the node from the second graphical representation, and
  - adding the first and second paths to the combined graph by adding one or more edges, in the combined graph, connecting to the combined node, wherein the combined graph distinguishes between the first and second rule sets by depicting the first path using a first color and the second path using a second color;
- obtain patient information comprising at least one clinical condition;
- search the combined graph based on the at least one clinical condition; and
- upon determining that the at least one path matching the at least one clinical condition is found in the combined graph:
  - highlight, in the combined graph, one or more nodes associated with the at least one path; and
  - determine a clinical conclusion based on the at least one path.

18. The computer program product of claim 17, wherein the combined graph is generated based on a plurality of graphical representations, wherein each of the plurality of graphical representations represents a respective rule set of the plurality of rule sets.

19. The computer program product of claim 18, wherein generating the combined graph further comprises:
combine two or more second nodes in different graphical representations indicating a same clinical conclusion.

20. The computer program product of claim 18, the program instructions executable by the processor cause the processor to:
- prompt, for each of the at least one path, a further first node in the path which indicates a further clinical condition not comprised in the patient information;
- in response to obtaining subsequent patient information comprising the further clinical condition, determine a path from the at least one path; and
- determine the clinical conclusion based on the determined path.

* * * * *